US008641610B2

(12) United States Patent
Okoniewski et al.

(10) Patent No.: US 8,641,610 B2
(45) Date of Patent: Feb. 4, 2014

(54) ACCESS ASSEMBLY WITH TRANSLATING LUMENS

(75) Inventors: Greg Okoniewski, North Haven, CT (US); Michael Bettuchi, Middletown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/223,627

(22) Filed: Sep. 1, 2011

(65) Prior Publication Data

US 2012/0157780 A1 Jun. 21, 2012

Related U.S. Application Data

(60) Provisional application No. 61/424,914, filed on Dec. 20, 2010.

(51) Int. Cl.
*A61B 17/02* (2006.01)

(52) U.S. Cl.
USPC .......................................... 600/207; 600/208

(58) Field of Classification Search
USPC .................................................. 600/201–246
See application file for complete search history.

(56) References Cited

U.S. PATENT DOCUMENTS

| 3,402,710 | A | 9/1968 | Paleschuck |
| 3,777,757 | A | 12/1973 | Gray et al. |
| 4,112,932 | A | 9/1978 | Chiulli |
| 5,209,741 | A | 5/1993 | Spaeth |
| 5,269,772 | A | 12/1993 | Wilk |
| 5,312,417 | A | 5/1994 | Wilk |
| 5,342,385 | A | 8/1994 | Norelli et al. |
| 5,391,156 | A | 2/1995 | Hildwein et al. |
| 5,395,367 | A | 3/1995 | Wilk |
| 5,454,367 | A * | 10/1995 | Moll et al. .................... 600/207 |
| 5,480,410 | A | 1/1996 | Cuschieri et al. |
| 5,490,843 | A | 2/1996 | Hildwein et al. |
| 5,507,758 | A | 4/1996 | Thomason et al. |
| 5,511,564 | A | 4/1996 | Wilk |
| 5,514,133 | A | 5/1996 | Golub et al. |
| 5,524,644 | A | 6/1996 | Crook |
| 5,545,150 | A | 8/1996 | Danks et al. |
| 5,634,911 | A | 6/1997 | Hermann et al. |
| 5,634,937 | A | 6/1997 | Millenauer et al. |
| 5,803,921 | A | 9/1998 | Bonadio |
| 5,830,191 | A | 11/1998 | Hildwein et al. |
| 5,833,603 | A | 11/1998 | Kovacs et al. |

(Continued)

FOREIGN PATENT DOCUMENTS

| CA | 2702419 | 11/2010 |
| EP | 1 312 318 | 5/2003 |

(Continued)

OTHER PUBLICATIONS

European Search Report 11194126.6-2310 dated Feb. 5, 2012.

(Continued)

*Primary Examiner* — Jerry Cumberledge

(57) ABSTRACT

An assembly for accessing a body cavity during a surgical procedure. The access assembly includes a compressible body having proximal and distal ends and a substantially hourglass-shaped central portion extending therebetween and includes first and second lumen extending therethrough. The access assembly further includes a translating mechanism operably positioned within the compressible body between the first and second lumen for selectively translating the first and second lumen relative to each other.

15 Claims, 5 Drawing Sheets

(56) References Cited

U.S. PATENT DOCUMENTS

| | | | |
|---|---|---|---|
| 5,904,703 A | 5/1999 | Gilson | |
| 5,906,577 A | 5/1999 | Beane et al. | |
| 5,911,757 A | 6/1999 | Seare, Jr. | |
| 6,004,303 A | 12/1999 | Peterson | |
| 6,033,426 A | 3/2000 | Kaji | |
| 6,048,309 A | 4/2000 | Flom et al. | |
| 6,440,063 B1 | 8/2002 | Beane et al. | |
| 6,486,588 B2 | 11/2002 | Doron et al. | |
| 6,551,270 B1 | 4/2003 | Bimbo et al. | |
| 6,562,022 B2 | 5/2003 | Hoste et al. | |
| 6,578,577 B2 | 6/2003 | Bonadio et al. | |
| 6,723,088 B2 | 4/2004 | Gaskill, III et al. | |
| 6,929,637 B2 | 8/2005 | Gonzalez et al. | |
| 7,008,377 B2 | 3/2006 | Beane et al. | |
| 7,011,645 B2 | 3/2006 | McGuckin, Jr. et al. | |
| 7,052,454 B2 | 5/2006 | Taylor | |
| 7,125,382 B2 | 10/2006 | Zhou et al. | |
| 7,297,112 B2 | 11/2007 | Zhou et al. | |
| 7,300,399 B2 | 11/2007 | Bonadio et al. | |
| 7,416,530 B2 | 8/2008 | Turner et al. | |
| 7,473,221 B2 | 1/2009 | Ewers et al. | |
| 7,559,893 B2 | 7/2009 | Bonadio et al. | |
| 7,563,250 B2 | 7/2009 | Wenchell | |
| 7,657,297 B2 | 2/2010 | Simpson et al. | |
| 7,686,762 B1 | 3/2010 | Najafi et al. | |
| 7,758,500 B2 | 7/2010 | Boyd et al. | |
| 7,766,824 B2 | 8/2010 | Jensen et al. | |
| 7,787,963 B2 | 8/2010 | Geistert et al. | |
| 7,798,998 B2 | 9/2010 | Thompson et al. | |
| 7,850,600 B1* | 12/2010 | Piskun | 600/114 |
| 8,033,995 B2* | 10/2011 | Cropper et al. | 600/207 |
| 8,157,786 B2 | 4/2012 | Miller et al. | |
| 8,187,177 B2 | 5/2012 | Kahle et al. | |
| 8,187,178 B2 | 5/2012 | Bonadio et al. | |
| 8,257,253 B2* | 9/2012 | Piskun | 600/208 |
| 2002/0019635 A1 | 2/2002 | Wenstrom, Jr. et al. | |
| 2003/0014076 A1 | 1/2003 | Mollenauer et al. | |
| 2003/0093104 A1 | 5/2003 | Bonner et al. | |
| 2004/0092795 A1 | 5/2004 | Bonadio et al. | |
| 2004/0236192 A1 | 11/2004 | Necola Shehada et al. | |
| 2005/0004478 A1 | 1/2005 | Fitz | |
| 2005/0096695 A1 | 5/2005 | Olich | |
| 2005/0165317 A1 | 7/2005 | Turner et al. | |
| 2006/0020241 A1 | 1/2006 | Piskun et al. | |
| 2006/0149306 A1 | 7/2006 | Hart et al. | |
| 2006/0161049 A1 | 7/2006 | Beane et al. | |
| 2006/0200012 A1 | 9/2006 | Mansour et al. | |
| 2006/0200220 A1 | 9/2006 | Brown et al. | |
| 2006/0247500 A1 | 11/2006 | Voegele et al. | |
| 2006/0247516 A1 | 11/2006 | Hess et al. | |
| 2006/0247673 A1 | 11/2006 | Voegele et al. | |
| 2006/0247678 A1 | 11/2006 | Weisenburgh, II et al. | |
| 2006/0270911 A1 | 11/2006 | Voegele et al. | |
| 2007/0027371 A1 | 2/2007 | Benaron et al. | |
| 2007/0060884 A1 | 3/2007 | Hayek | |
| 2008/0027476 A1 | 1/2008 | Piskun | |
| 2008/0033273 A1 | 2/2008 | Zhou et al. | |
| 2008/0058652 A1 | 3/2008 | Payne | |
| 2008/0058728 A1 | 3/2008 | Soltz et al. | |
| 2008/0097332 A1 | 4/2008 | Greenhalgh et al. | |
| 2008/0108885 A1 | 5/2008 | Colvin, Jr. | |
| 2008/0154101 A1 | 6/2008 | Jain et al. | |
| 2008/0161826 A1 | 7/2008 | Guiraudon | |
| 2008/0188868 A1 | 8/2008 | Weitzner et al. | |
| 2008/0255519 A1 | 10/2008 | Piskun et al. | |
| 2008/0287788 A1 | 11/2008 | Richardson et al. | |
| 2009/0054908 A1 | 2/2009 | Zand et al. | |
| 2009/0093752 A1 | 4/2009 | Richard et al. | |
| 2009/0093850 A1 | 4/2009 | Richard | |
| 2009/0163782 A1 | 6/2009 | Shehada et al. | |
| 2009/0209969 A1 | 8/2009 | Wolfe | |
| 2009/0299153 A1 | 12/2009 | Gerber et al. | |
| 2010/0063452 A1 | 3/2010 | Edelman et al. | |
| 2010/0081880 A1* | 4/2010 | Widenhouse et al. | 600/201 |
| 2010/0081895 A1 | 4/2010 | Zand | |
| 2010/0100043 A1 | 4/2010 | Racenet | |
| 2010/0240960 A1 | 9/2010 | Richard | |
| 2010/0249523 A1 | 9/2010 | Spiegal et al. | |
| 2010/0249524 A1 | 9/2010 | Ransden et al. | |
| 2010/0280326 A1 | 11/2010 | Hess et al. | |
| 2010/0286484 A1 | 11/2010 | Stellon et al. | |
| 2010/0298646 A1 | 11/2010 | Stellon et al. | |
| 2010/0312060 A1* | 12/2010 | Widenhouse et al. | 600/201 |
| 2010/0312065 A1* | 12/2010 | Shelton et al. | 600/207 |
| 2011/0028891 A1 | 2/2011 | Okoniewski | |
| 2011/0034778 A1 | 2/2011 | Kleyman | |
| 2011/0054257 A1 | 3/2011 | Stopek | |
| 2011/0054258 A1 | 3/2011 | O'Keefe et al. | |
| 2011/0054260 A1 | 3/2011 | Albrecht et al. | |
| 2011/0082341 A1 | 4/2011 | Kleyman et al. | |
| 2011/0082343 A1* | 4/2011 | Okoniewski | 600/208 |
| 2011/0082346 A1 | 4/2011 | Stopek | |
| 2011/0125186 A1 | 5/2011 | Fowler et al. | |
| 2011/0166423 A1 | 7/2011 | Farascioni et al. | |
| 2011/0190590 A1* | 8/2011 | Wingardner et al. | 600/208 |
| 2012/0022334 A1* | 1/2012 | Piskun | 600/208 |

FOREIGN PATENT DOCUMENTS

| | | |
|---|---|---|
| EP | 1312318 | 5/2003 |
| EP | 2 044 889 | 4/2009 |
| EP | 2 095 781 | 9/2009 |
| EP | 2 098 182 | 9/2009 |
| EP | 2 229 900 | 9/2010 |
| EP | 2226025 | 9/2010 |
| EP | 2229900 | 9/2010 |
| EP | 2 238 924 | 10/2010 |
| EP | 2 238 925 | 10/2010 |
| EP | 2 248 478 | 11/2010 |
| EP | 2 253 283 | 11/2010 |
| EP | 2253283 | 11/2010 |
| EP | 2 272 450 | 1/2011 |
| EP | 2 292 165 | 3/2011 |
| WO | WO 93/14801 | 8/1993 |
| WO | WO 2004/054456 | 7/2004 |
| WO | WO 2008/121294 | 10/2008 |
| WO | WO2009/036343 | 3/2009 |
| WO | WO 2009/036343 A1 | 3/2009 |
| WO | WO 2010/141409 | 12/2010 |

OTHER PUBLICATIONS

European Search Report 11250792.6-310 dated Feb. 24, 2012.
European Search Report for corresponding EP11194244 date of mailing is Mar. 20, 2012 (5 pgs).
European Search Report for EP 11194244.7-1269 date of completion is Mar. 14, 2012 (5 pages).

* cited by examiner

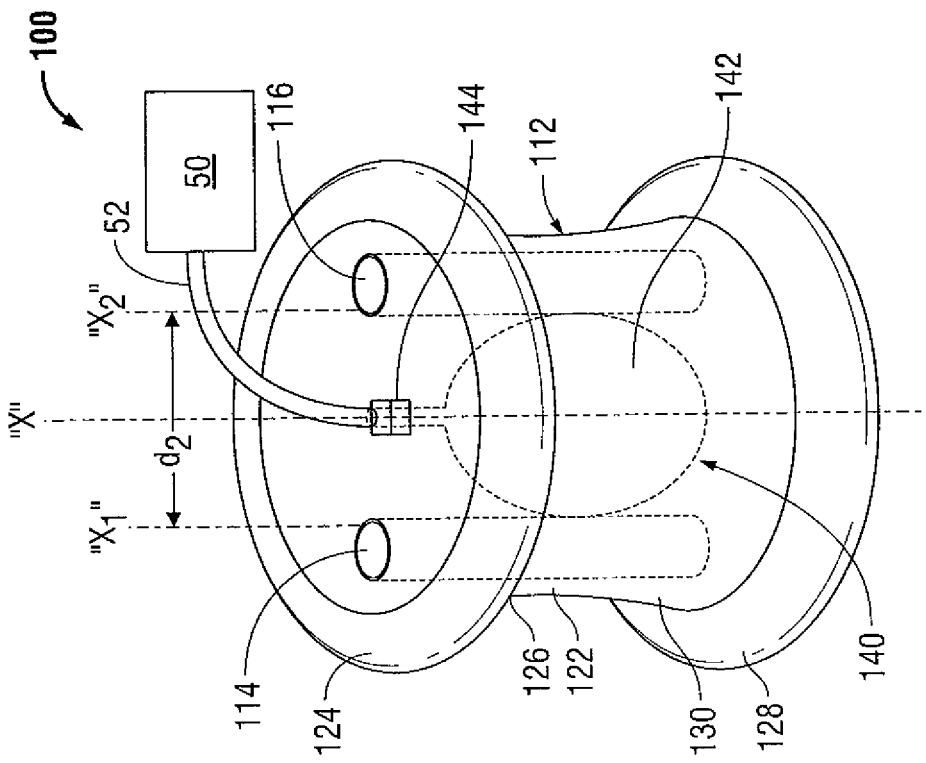
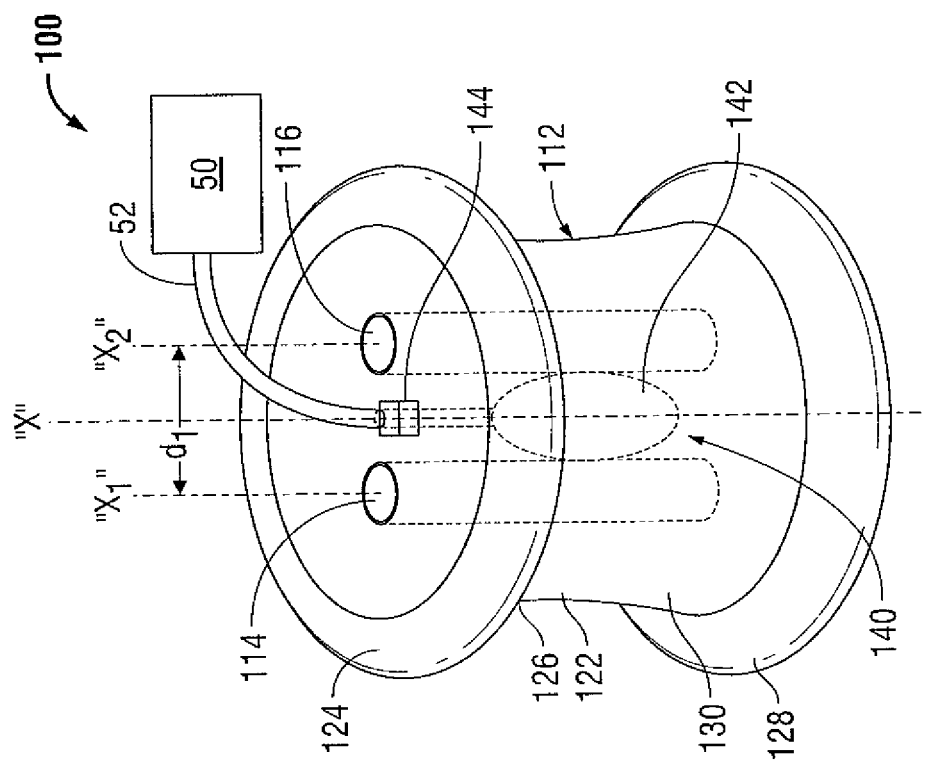

ACCESS ASSEMBLY WITH TRANSLATING LUMENS

CROSS REFERENCE TO RELATED APPLICATION

The present application claims the benefit of and priority to U.S. Provisional Application Ser. No. 61/424,914 filed on Dec. 20, 2010, the entire contents of which are incorporated herein by reference.

BACKGROUND

1. Technical Field

The present disclosure relates to a flexible access assembly for use in surgical procedures. More particularly, the present disclosure relates to an access assembly including a translating mechanism for adjusting the configuration of the lumens extending through the assembly.

2. Background of Related Art

Access assemblies configured for reception through an incision into an abdominal cavity are known, as are methods of inserting the access assemblies therethrough. Traditional access assemblies include a rigid cannula that is received through the tissue of the body wall into the body cavity. Endoscopic, laparoscopic and other suitable instruments may then be directed through a housing on the proximal end of the cannula to access the body cavity in a sealing manner through the access assembly.

Compressible assemblies configured for accessing a body cavity and permitting reception of instruments therethrough in sealing manner are also known. Such compressible assemblies are composed of silicone, thermoplastic elastomers (TPE), rubber, foam, gel and other compressible materials and are configured to be compressed to facilitate insertion into an opening in tissue, for example, an incision. Typically, such assemblies are deformed by a surgeon using his/her fingers or with the assistance of a grasping device, e.g., forceps. Compression of the assembly reduces the profile of the assembly, thereby facilitating reception of the assembly into the opening. Upon release of the compressive force, the compressed assembly returns to an uncompressed configuration. In the uncompressed configuration, the access assembly seals the incision into the body cavity. The assembly may have one or more access lumen for receiving instruments therethrough and may optionally be configured for connection with a source of insufflation gas.

Typically, the two or more lumens that extend through the access assembly are configured to receive instruments therethrough in a sealed manner. These lumens are generally fixed relative to one another and extend through the access assembly in a parallel or angled configuration. Although the access assemblies are typically configured such that instruments inserted therethrough may be individually manipulated relative to each other and the longitudinal axis, excessive manipulation of the instruments may compromise the seal between the instrument and the assembly and/or between the assembly and the body cavity.

Therefore, it is desirable to provide an access assembly which includes lumens capable of being translated within the access assembly.

SUMMARY

Accordingly, an access assembly including translating lumen is provided. For example, in an embodiment, the present invention relates to an access assembly comprising: a compressible body having proximal and distal ends and a substantially hourglass-shaped central portion extending therebetween and including first and second lumen extending therethrough; and a translating mechanism operably positioned within the compressible body between the first and second lumen for selectively translating the first and second lumen relative to each other. The translating mechanism may include an inflatable member, a pair of inflatable members, a drive shaft and a pair of links. The access assembly may include one or more additional lumen. In an embodiment, the first lumen may be spaced a first distance from the second lumen when the translating mechanism is in a first configuration. The first lumen may be spaced a second distance from the second lumen when the translating mechanism is in a second configuration. The first and second lumens may be parallel to one another or the first lumen may be at an angle with respect to the second lumen.

In another embodiment, the present invention relates to a method of accessing a body cavity. The method may comprise the steps of: providing an access assembly having a translating mechanism for selectively translating first and second lumens extending therethrough; receiving the access assembly through an opening in tissue; activating the translating mechanism to selectively translate at least one of the first and second lumens; and manipulating one or more instruments through the first and second lumens to complete a procedure. The method may also include the step of reactivating the translating mechanism to further selectively translate at least one of the first and second lumens. The translating mechanism may include an inflatable member, and the step of activating the translating mechanism may include providing inflation gas to the inflatable member.

DESCRIPTION OF THE DRAWINGS

Embodiments of a flexible access assembly are disclosed herein with reference to the drawings, wherein:

FIG. 1 is a perspective view of an embodiment of an access assembly according to the present disclosure, including a translating mechanism is in a first condition;

FIG. 2 is a perspective view of the access assembly of FIG. 1, including the translating mechanism is in a second condition;

DETAILED DESCRIPTION

Embodiments of the presently disclosed access assembly will now be described in detail with reference to the drawings wherein like numerals designate identical or corresponding elements in each of the several views. As is common in the art, the term "proximal" refers to that part or component closer to the user or operator, e.g. surgeon or physician, while the term "distal" refers to that part or component further away from the user. Although the access assemblies of the present disclosure will be described as relates to accessing an abdominal cavity through an incision in the abdominal wall, the access assemblies of the present disclosure may be modified for use in other closed procedures, e.g., laparoscopic, arthroscopic, endoscopic. Furthermore, the access assemblies of the present disclosure may be modified for use in accessing internal cavities through natural orifices, e.g., anus, vagina.

Referring initially to FIG. 1, an access assembly according to an embodiment of the present disclosure is shown generally as access assembly 100. Access assembly 100 is flexible and/or compressible to allow for insertion through an incision in tissue into a body cavity or through an opening in the body of a patient, e.g., anus, such that after insertion, access assembly 100 creates a seal within the incision/opening through which a surgeon may insert and manipulate one or more surgical instruments to complete a procedure.

Figure 3:
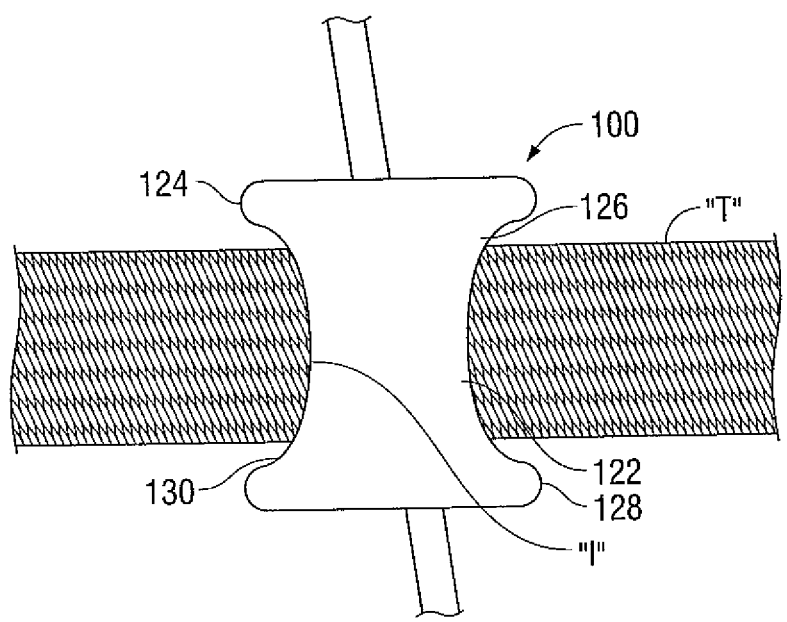
FIG. 3 is a perspective view of the access assembly of FIGS. 1 and 2 inserted through tissue.

With reference to FIGS. 1 and 2, access assembly 100 includes a body 112 defining a substantially hourglass shape when viewed from the side. Access assembly 100 defines a longitudinal axis "X" extending therethrough. Body 112 includes a central portion 122 having an upper rim 124 located at a proximal end 126 of central portion 122 and a lower rim 128 located at a distal end 130 of central portion 122. Central portion 122 is configured to span the thickness of tissue "T" (FIG. 5) (FIG. 3). Upper rim 124 and lower rim 128 aid in preventing movement of access assembly 100 longitudinally through incision "I" (FIG. 5) (FIG. 3). As the thickness of tissue depends on the body composition of the patient and the location through which the underlying cavity is being accessed, the length and size of access assembly 100 may be modified to suit a given procedure.

Still referring to FIGS. 1 and 2, body 112 of access assembly 100 may be formed of various materials such as, for example, silicone, thermoplastic elastomers (TPE), rubber, foam, gel, etc. In this manner, access assembly 100 may be compressed or squeezed prior to insertion through an incision or natural orifice in the body of a patient. In one embodiment, body 112 includes TPE material that is infused with an inert gas, e.g. $CO_2$ or Nitrogen, to form a foam structure. Body 112 may be coated with a lubricant, e.g. Parylene N or C, in order to create a lubricious surface. Various other coatings, e.g., hydrophilic, hydrophobic, bio-agents, anti-infection, analgesic, may also be employed to improve the access assembly or to adapt access assembly 100 for a specific procedure.

Figure 9:
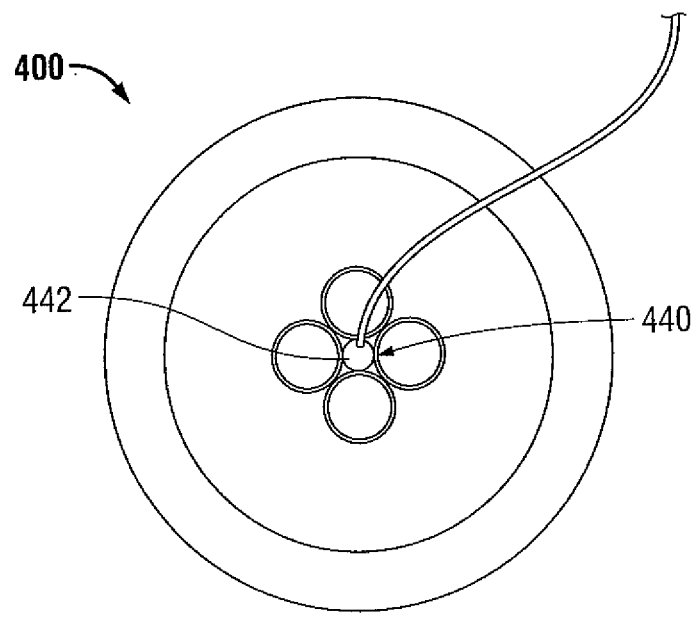
FIG. 9 is a top view of an access assembly according to still yet another embodiment of the present disclosure, including a translating mechanism in a first condition.
Figure 10:
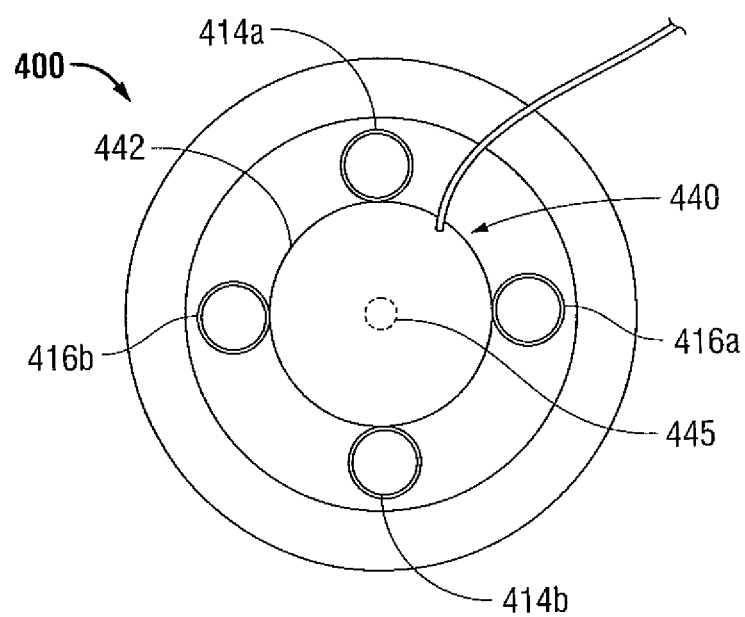
FIG. 10 is a top view of an access assembly according to FIG. 9, including a translating mechanism in a second condition.

With reference still to FIGS. 1 and 2, body 112 of access assembly 100 defines a plurality of lumen 114, 116. As shown, access assembly 100 includes a pair of lumen 114, 116 having substantially similar size and shape for receiving instruments of substantially similar diameter. Alternatively, lumens 114, 116 may differ in size and/or cross-sectional profile for receiving instruments of other configurations. Although shown including a pair of lumen, it is envisioned that access assembly 100 may include three or more lumens. (FIGS. 9 and 10). Lumens 114, 116 extend through central portion 122 of body 112 and define longitudinal axes "$X_1$", "$X_2$", respectively, configured to receive surgical instruments, cannula assemblies, valve assemblies and/or insufflation apparatus. Lumens 114, 116 may include a protective lining extending along at least a portion of the length of central portion 122 to prevent tearing of access assembly 100 as instruments "I" (FIG. 3) are manipulated therethrough.

Lumens 114, 116 may also be coated with a lubricant to assist in insertion of surgical instruments therethrough.

Still referring to FIGS. 1 and 2, access assembly 100 further includes a translating mechanism 140 operably positioned between lumens 114, 116. Translating mechanism 140 is configured to laterally translate lumens 114, 116 within access assembly 100. In one embodiment, and as shown in FIGS. 1 and 2, translating mechanism 140 includes an inflatable member 142 operably connected to a source of inflation gas 50 by an inflation hose 52. Inflation source 50 may be permanently or selectively connected to access assembly 100. Translating mechanism 140 may include a valve member 144 configured to maintain an inflation gas within inflatable member 142. In this manner, once inflatable member 142 has been inflated such that lumens 114, 116 are appropriately spaced, inflation gas source 50 may be disconnected from inflatable member 142. Inflation gas source 50 may be reconnected in the event that further inflation of inflatable member 142 is desired. Valve member 144 may further be configured to permit the selective release of inflation gas from within inflatable member 142.

With particular reference to FIG. 1, when inflatable member 142 is in a first or deflated condition, lumens 114, 116 are spaced apart a first distance "d1". In the first condition, lumens 114, 116 are in close proximity to one another, thereby permitting a surgeon to manipulate a first instrument (not shown) through lumen 114 and a second instrument (not shown) through lumen 116 while having the distal ends of each of the first and second instruments in close proximity to each other. For example, in a suture tying procedure, it would be advantages to have the distal ends of a first and second instrument in close proximity to other.

Turning now to FIG. 2, when inflatable member 142 is in a second or inflated condition, lumens 114, 116 are spaced apart a second distance "d2". In the inflated condition, lumens 114, 116 are spaced apart from each other, thereby permitting a surgeon more room to manipulate a first instrument (not shown) through lumen 114 and a second instrument (not shown) through lumen 116 as the distal ends of each of the first and second instruments are spaced apart from each other. Partial inflation of inflatable member 142 causes translation of lumens 114, 116 to a distance between first and second distances "d1", "d2". As shown, in both the inflated and deflated conditions, lumens 114, 116 remain parallel to each other.

In one embodiment, inflatable member 142 may comprise a pair of inflatable members (not shown) extending along longitudinal axis "X". Inflation of a first of the inflatable members translates lumen 114 away from longitudinal axis "X" while inflation of the second of the inflatable members translates lumen 116 away from longitudinal axis "X". In this manner, lumens 114, 116 may be moved independently relative to longitudinal axis "X".

With reference now to FIGS. 1-3, in use, access assembly 100 is inserted through tissue "T" by compressing body 112 and inserting distal end 130 thereof through incision/opening "I". Release of the compressive force on body 112 allows body 112 to return to an uncompressed condition within incision "I", thereby creating a seal with tissue "T". As discussed above, upper and lower rims 124, 128, respectively, maintain access assembly 100 within tissue "T". Although typically inserted through incision "I" with inflatable member 142 in the first or deflated condition, it is envisioned that inflatable member 142 may be partially or fully inflated prior to insertion.

Once access assembly 100 is received within incision "I", inflation member 142 is inflated until lumens 114, 116 are spaced an appropriate distance from one another for the procedure being performed. Once lumens 114, 116 are properly positioned, access assembly 100 may be used as a conventional access assembly. At any point during the procedure, inflation gas source 50 may be used to provide additional inflation gas to inflatable member 142 to further translate lumens 114, 116 apart from each other. Alternatively, valve member 144 may be activated to cause the release of inflation gas from inflatable member 142 to cause the translation of lumens 114, 116 toward each other.

Figure 5:
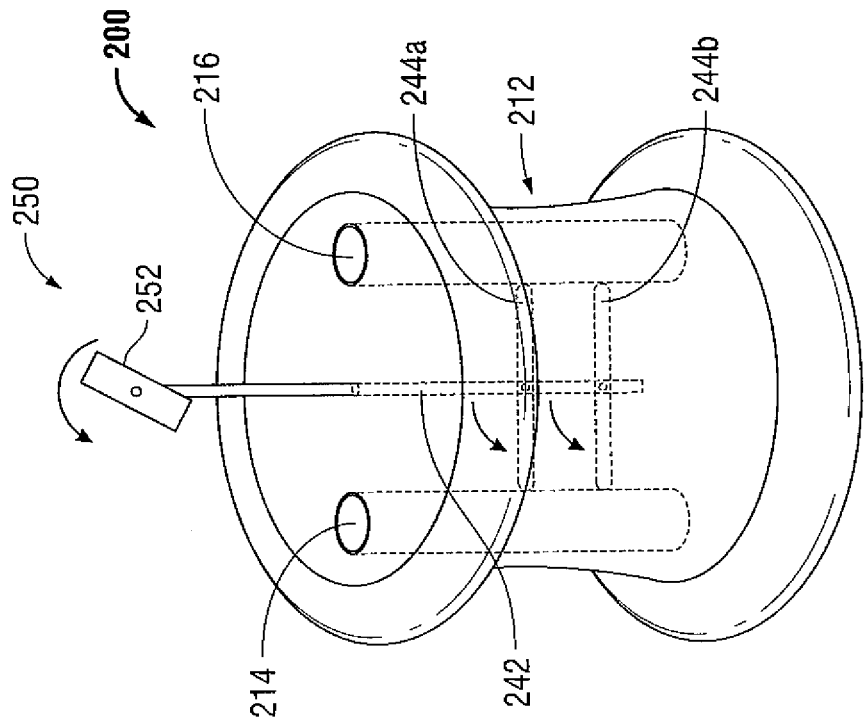
FIG. 5 is a perspective view of the access assembly of FIG. 4, including the translating mechanism is in a second condition.
Figure 4:
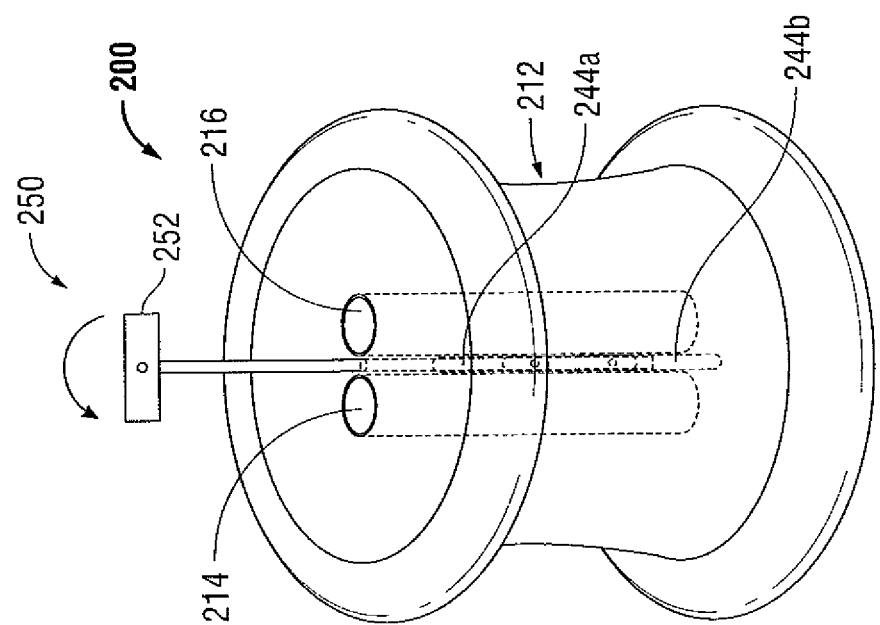
FIG. 4 is a perspective view of another embodiment of an access assembly according to the present disclosure, including a translating mechanism is in a first condition.

Turning now to FIGS. 4 and 5, an alternative embodiment of an access assembly according to the present disclosure is shown generally as access assembly 200. Access assembly 200 is substantially similar to access assembly 100 described hereinabove, and will only be described as relates to the differences therebetween. Access assembly 200 includes a body 212 defining a pair of lumen 214, 216. A translating mechanism 240 is positioned between lumens 214, 216. Translating mechanism 240 includes a drive shaft 242 and a pair of links 244a, 244b. Links 244a, 244b are pivotally connected to drive shaft 242 and are rotatable between a first position and a second position. Translating mechanism 240 further includes drive mechanism 250 operably connected to drive shaft 242 for causing the rotation of links 244a, 244b. Drive mechanism 250 may include a handle member 252, as shown, for manual operation rotation of links 244a, 244b. Alternatively, drive mechanism 250 may include an electric or pneumatic powered drill or other device.

With particular reference to FIG. 4, in the first position, links 244a, 244b are pivoted such that links 244a, 244b extend along drive shaft 242. In this manner, lumens 214, 216 are positioned substantially adjacent one another. Turning to FIG. 5, in the second position, links 244a, 244b are pivoted ninety degrees (90°) relative to drive shaft 242. In this manner, lumens 214, 216 are approximated away from each other. Translating mechanism 240 is configured to pivot links 244a, 244b anywhere between zero and ninety degrees (0-90°) relative to drive shaft 242. Thus, lumens 214, 216 may be spaced relative to drive shaft 242 any distance from the initial position in FIG. 4 to the second position FIG. 5.

Although shown as pivoting simultaneously, and thus, maintaining lumens 214, 216 parallel throughout translation and/or use, it is envisioned that translating mechanism 240 may be configured to pivot links 244a, 244b independently of one another. In this manner, lumens 214, 216 may be translated at an angle relative to each other and drive shaft 242.

Figure 8:
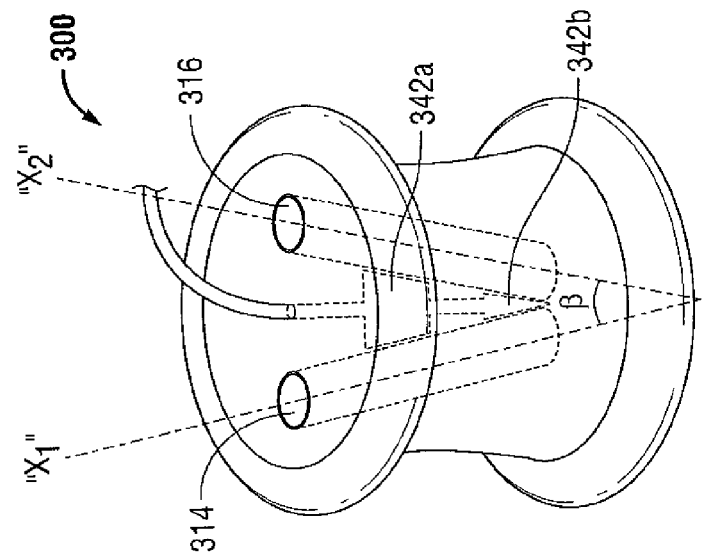
FIGS. 7 and 8 are perspective views of the access assembly of FIG. 6, including the translating mechanism in subsequent conditions.
Figure 7:
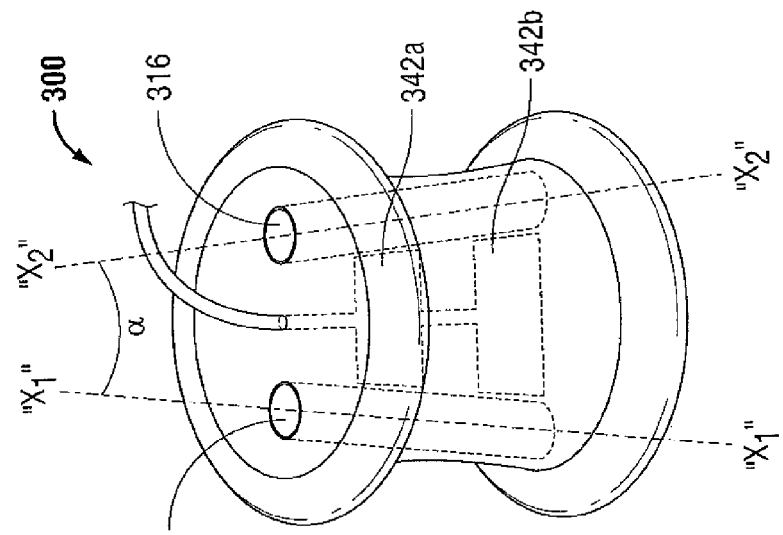
Figure 6:
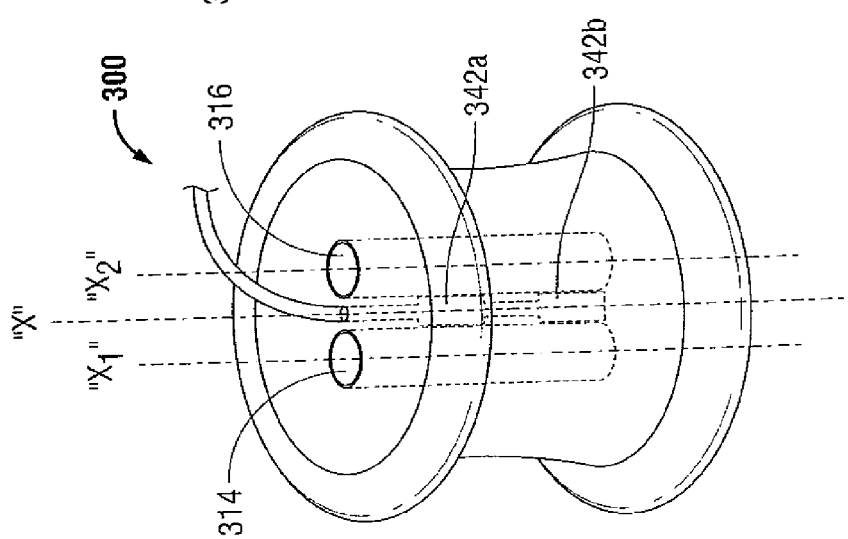
FIG. 6 is a perspective view of an access assembly according to yet another embodiment of the present disclosure, including a translating mechanism in a first condition.

Turning now to FIGS. 6-8, another access assembly according to an embodiment of the present disclosure is shown generally as access assembly 300. Access assembly 300 includes a pair of lumen 314, 316 and a translating mechanism 340 received therebetween. Translating mechanism 340 includes a pair of inflation members 342a, 342b spaced along longitudinal axis "X". Each of inflation members 342a, 342b may be inflated independent of the other. In this manner, lumens 314, 316 may be translated at an angle relative to each other. As shown in FIG. 7, inflation of second inflation member 342b to a greater degree than inflation of first inflation member 342a causes lumens 314, 316 to extend at an angle α relative to each other. As shown in FIG. 8, inflation of first inflation member 342a to a greater degree than inflation of second inflation member 342b causes lumens 314, 316 to extend at an angle β relative to each other.

With reference now to FIGS. 9 and 10, yet another embodiment of an access assembly according to the present disclosure is shown generally as access assembly 400. Access assembly 400 includes two pair of lumen 414a, 414b, 416a, 416b and a translating mechanism 440 operably positioned therebetween. Translating mechanism 440 includes an inflatable member 442. Inflatable member 442 is configured to radially expand from a first or deflated condition (FIG. 9) to a second or inflated condition (FIG. 10). It is envisioned that inflatable member 442 may include a cylindrical, conical or frustro-conical configuration. As inflatable member 442 radially expands, pairs of lumens 414a, 414b, 416a, 416b are translated away from each other in a manner similar to that described above. It is envisioned that inflatable member 442 may include a passageway 445 configured for receipt of one or more surgical instruments.

It will be understood that various modifications may be made to the embodiments disclosed herein. For example, as noted hereinabove, the disclosed flexible access assembly may be provided with multiple lumens, in excess of the disclosed four lumens. Additionally, the diameters or configuration of the disclosed lumen need not be identical but may be varied depending upon the contemplated surgical instruments to be utilized therethrough. Therefore, the above description should not be construed as limiting, but merely as exemplifications of particular embodiments. Those skilled in the art will envision other modifications within the scope and spirit of the claims appended hereto.

The invention claimed is:

1. An access assembly comprising:
   a compressible body having proximal and distal ends and a substantially hourglass-shaped central portion extending therebetween and including first and second lumens extending therethrough, the first lumen defining a first central longitudinal axis and the second lumen defining a second central longitudinal axis; and
   a translating mechanism, separate from the compressible body and operably positioned within the compressible body between the first and second lumens for selectively translating at least one of the first and second lumens relative to each other in a lateral direction between a first position where the first and second central longitudinal axes have a first distance between them and a second position where the first and second central longitudinal axes have a second distance between them, wherein the first distance is less than the second distance.

2. The access assembly of claim 1, wherein the translating mechanism includes an inflatable member.

3. The access assembly of claim 2, wherein the translating mechanism includes a pair of inflatable members.

4. The access assembly of claim 1, wherein the translating mechanism includes a drive shaft and a pair of links.

5. The access assembly of claim 1, further including one or more additional lumen.

6. The access assembly of claim 1, wherein the first central longitudinal axis is spaced the first distance from the second central longitudinal axis when the translating mechanism is in a first configuration.

7. The access assembly of claim 1, wherein the first central longitudinal axis is spaced the second distance from the second central longitudinal axis when the translating mechanism is in a second configuration.

8. The access assembly of claim 1, wherein the first and second lumens are parallel to one another.

9. The access assembly of claim 1, wherein the first lumen is at an angle with respect to the second lumen.

10. The access assembly of claim 1, wherein fluid flow between the proximal and distal ends is directed through only the first and second lumens when the first and second lumens are in the first position and the second position.

11. The access assembly of claim 1, wherein the first and second lumens are formed through the compressible body.

12. The access assembly of claim 1, wherein the compressible body defines a seal between the proximal and distal ends when the lumens are in the first position and in the second position.

13. The access assembly of claim 1, wherein the first and second lumens maintain their internal dimensions when translated between the first and second positions.

14. An access assembly comprising:
   a compressible body having proximal and distal ends and a substantially hourglass-shaped central portion extending therebetween and including first and second lumens extending therethrough, the first lumen defining a first central longitudinal axis and the second lumen defining a second central longitudinal axis; and
   a translating mechanism, including a pair of members, operably positioned within the compressible body between the first and second lumens for selectively translating at least one of the first and second lumens relative to each other in a lateral direction between a first position where the first and second central longitudinal axes have a first distance between them and a second position where the first and second central longitudinal axes have a second distance between them, wherein the first distance is less than the second distance.

15. The access assembly of claim 14, wherein the translating mechanism includes a drive shaft and the pair of members is a pair of links pivotable about the drive shaft.

\* \* \* \* \*